United States Patent [19]

Rattan

[11] Patent Number: 5,371,089
[45] Date of Patent: Dec. 6, 1994

[54] METHOD AND COMPOSITION FOR AMELIORATING THE ADVERSE EFFECTS OF AGING

[75] Inventor: Suresh I. S. Rattan, Aarhus, Denmark

[73] Assignee: Senetek, PLC, St. Louis, Mo.

[21] Appl. No.: 206,041

[22] Filed: Mar. 4, 1994

Related U.S. Application Data

[60] Continuation of Ser. No. 954,614, Sep. 30, 1992, abandoned, which is a continuation-in-part of Ser. No. 611,903, Nov. 9, 1990, abandoned, which is a division of Ser. No. 19,150, Feb. 26, 1987, abandoned, and a continuation of Ser. No. 954,614, Sep. 30, 1992, abandoned.

[51] Int. Cl.$^5$ ............................................. A61K 31/52
[52] U.S. Cl. ................................... 514/261; 514/266; 514/844
[58] Field of Search ..................... 514/261, 266, 844

[56] References Cited

U.S. PATENT DOCUMENTS

| | | | |
|---|---|---|---|
| 3,126,318 | 3/1964 | Legator | 167/65 |
| 4,581,056 | 4/1986 | Nooden et al. | 71/28 |
| 4,610,978 | 9/1986 | Dikstein et al. | 514/46 |
| 4,853,386 | 8/1989 | Friebe et al. | 514/266 |
| 5,021,422 | 6/1991 | Bolund et al. | 514/261 |
| 5,151,425 | 9/1992 | Clark | 514/261 |

FOREIGN PATENT DOCUMENTS

| | | |
|---|---|---|
| 632589 | 11/1963 | Belgium . |
| 0103878 | 3/1984 | European Pat. Off. . |
| 1587633 | 3/1970 | France . |
| 148889 | 7/1981 | German Dem. Rep. . |
| 47-26687 | 7/1972 | Japan . |
| 0006616 | 6/1983 | Japan . |
| 60-19709 | 1/1985 | Japan . |

OTHER PUBLICATIONS

Bindra "Anti-Aging Drugs" in *Burger's Medicinal Chemistry*, Part III, pp. 1–9 1981.
Orr et al., "The effects of kinetin upon epithelium and fibroblasts in tissue culture," *Cancer*, 10:617–624 (1957).
Johnson et al., "N$^6$-substituted adenines induce cell elongation irrespective of the intracellular cyclic AMP levels," *Exper. Cell Res.*, 85:47–56 (1974).
Hecht et al., "Competitive inhibition of beef heart cyclic AMP phosphodiesterase by cytokinins and related compounds," *Proc. Natl. Acad. Sci. USA*, 71:4670–4674 (1974).
Mookerjee et al., "Effects of plant cytokinins on human lumphocyte transformation," *J. Reticuloendothel. Soc.*, 25:299–314 (1979).
Sacchi et al., "Changes in form of Elongation Factor 1 during germination of wheat seeds," *Eur. J. Biochem.*, 139:1–4 (1984).
Spirin et al., "Informosomes and polybribosome-associated proteins in eukaryotes," *Trends in Biochem. Sci.*, 10:162–164 (1985).

(List continued on next page.)

Primary Examiner—Gregory Hook
Attorney, Agent, or Firm—Fitch, Even, Tabin & Flannery

[57] ABSTRACT

Compositions and methods are provided for countering the adverse effects of aging on cells in culture and in vivo in which cells are contacted with the compositions that ameliorate the adverse effects of aging on mammalian cells by slowing or reversing the changes that normally accompanying aging of such cells but do not significantly increase the growth rate or total proliferative capacity of such cells. The compositions contain one or more 6-(substituted amino)purine cytokinins and preferably do not contain ingredients that promote cell division or that induce or potentiate the ability of the 6-(substituted amino) purine cytokinins to promote cell division.

Among the preferred applications of the compositions and methods provided herein are the preservation of or restoration of the health of mammalian cells in culture and, by application of the compositions to human skin, the health and youthful appearance of the skin.

20 Claims, No Drawings

OTHER PUBLICATIONS

Vesely et al., "Plant growth-promoting hormones activate mammalian guanylate cyclase activity," *Endocrinology*, 116:1887–1892 (1985).

Gordon et al., "6-substituted purines: A novel class of inhibitors of endogenous protein degradation in isolated rat hepatocytes," *Arch. Biochem. Biophys.*, 217:282–294 (1982).

*The Merck Index: An Encyclopedia of Chemicals and Drugs*, 9th Ed., Merck & Co., Inc., Rahway, N.J., M. Windholz, Ed.; p. 696 (1976).

Weiss et al., "Topical tretinoin improves photoaged skin: A double-blind vehicle-controlled study," *JAMA*, 259(4):527–532 (1988).

Kligman et al., "The contributions of UVA and UVB to connective tissue damage in hairless mice," *J. Investigative Dermatology*, 84:272–276 (1985).

Bissett et al., "An animal model of solar-aged skin: Histological, physical, and visible changes in UV-irradiated hairless mouse skin," *Photochem. and Photobiol.*, 46(3):367–378 (1987).

Kligman et al., "Collagen metabolism in ultraviolet irradiated hairless mouse skin and its correlation to histochemical observations," *J. Investigative Dermatology*, 23(2):210–214 (Aug. 1989).

Schwartz, E., "Connective tissue alternations in the skin of ultraviolet irradiated hairless mice," *J. Investigative Deermatology*, 91(2):158–161 (1988).

Warren et al., "Age, sunlight, and facial skin: A histologic and quantitative study," *J. Amer. Acad. of Dermatology*, 25:751–760 (1991).

Bissett et al., "Wavelength dependence of histological, physical, and visible changes in chronically UV-irradiated hairless mouse skin," *Photochem. and Photobiol.*, 50(6):763–769 (1989).

Schwartz et al., "Topical all-trans retinoic acid stimulates collagen synthesis in vivo," *J. of Investigative Dermatology*, 96(6):975–978 (1991).

Katsaros et al., "Site-selective cyclic AMP analogs provide a new approach in the control of cancer cell growth," *FEBS Letters*, 223(1):97–102 (1987).

Wainfan et al., "Inhibition of transfer ribonucleic acid methylating enzymes by cytotoxic analogs of adenosine," *Biochem. Pharmacology*, 22:493–500 (1973).

Kligman et al., "Long-term histologic follow-up of phenol face peels," *Plastic and Reconstructive Surgery*, 75(5):652–659 (1985).

Stegman, S., "A comparative histologic study of the effects of three peeling agents and dermabrasion on normal and sundamaged skin," *Aesthetic Plastic Surgery*, 6:123–135 (1982).

Braverman et al., "Studies in cutaneous aging: I. The elastic fiber network," *J. of Investigative Dermatology*, 78:434–443 (1982).

Bryce et al., "Retinoic acids promote the repair of the dermal damage and the effacement of wrinkles in the UVB-irradiated hairless mouse," *J. of Investigative Dermatology*, 91(2):175–180 (1988).

Ethier et al., "Aging increases adenosine and inosine release by human fibroblast cultures," *Mechanisms of Ageing and Development*, 50:159–168 (1989).

Bissett et al., "Photoprotective effect of topical anti-inflammatory agents against ultraviolet radiation-induced chronic skin damage in the hairless mouse," *Photodermatol. Photoimmunol. Photomed.*, 7:153–158 (1990).

METHOD AND COMPOSITION FOR AMELIORATING THE ADVERSE EFFECTS OF AGING

This application is a continuation of application Ser. No. 07/954,614, filed Sep. 30, 1992, now abandoned, which is a continuation-in-part of application Ser. No. 07/611,903, filed Nov. 9, 1990, now abandoned, which is a divisional of application Ser. No. 07/019,150, filed Feb. 26, 1987, now abandoned. This application is also a continuation of Ser. No. 07/954,614, filed Sep. 30, 1992, now abandoned, which is a continuation-in-part of PCT International Application No. PCT/US91/03466, filed May 16, 1991.

U.S. application Ser. Nos. 07/611,903 and 07/019,150 and PCT International Application No. PCT/US91/03466 are herein incorporated in their entirety by reference thereto.

TECHNICAL FIELD

Methods and compositions for ameliorating the adverse effects of aging in mammalian cells without increasing growth rate or total proliferative capacity of the cells are provided. More specifically, methods and compositions for countering the adverse effects of aging on mammalian cells in culture and in vivo, including cells of human skin, by contacting the cells with compositions containing 6-(substituted amino)purine cytokinins are provided.

BACKGROUND OF THE INVENTION

Cellular aging or cellular senescence is a universal attribute of normal non-transformed cells that is manifested by morphological changes accompanied by an age-dependent loss of proliferative potential, including the failure of the cells to respond to exogenous growth factors. A variety of theories have been proposed to explain the phenomenon of cellular senescence. Experimental evidence suggests that the age-dependent loss of proliferative potential may be the function of a genetic program (see, e.g., Smith et al. (1980) *Mech. Age. Dev.* 13:387; and Kirkwood et al. (1975) *Theor. Biol.* 53:481). This evidence includes cell fusion studies with human fibroblasts in vitro that demonstrate that the quiescent cellular senescent phenotype is dominant over the proliferative phenotype (see, e.g., Pereira-Smith et al. (1982) *Somatic Cell Genet.* 8:731; and Norwood et al. (1974) *Proc. Natl. Acad. Sci. U.S.A.* 71:223) and that protein synthesis in senescent cells, prior to fusion with young cells, is required for the inhibition of DNA synthesis within the young nucleus of the heterodikaryon (see, e.g., Burmer et al. (1983) *Exp. Cell Res.* 145:708; and Drescher-Lincoln et al. (1984) *Exp. Cell Res.* 153:208). Also, microinjection of senescent fibroblast mRNA into young fibroblasts inhibits the ability of the young cell to synthesize DNA (see, e.g., Lumpkin et al. (1986) *Science* 232:393) and entry of the young cell into the S phase of the cell cycle (Lumpkin et al. (1985) *Exp. Cell Res.* 160:544). Further, unique mRNA species are amplified in senescent fibroblasts in vitro (see, e.g., Wellinger et al. (1986) *J. Cell Biol.* 34:203; Flemming et al. (1988) *Proc. Natl. Acad. Sci. U.S.A.* 85:4099; West et al. (1989) *Exp. Cell Res.* 184:138; and Giordano (1989) *Exp. Cell Res.* 185:399). It has also been suggested that an altered genetic program exists in senescent human fibroblasts, which involves the repression of c-fos expression at the transcriptional level (see, e.g., Seshadri et al. (1990) *Science* 247:205). Thus, there appear to be genotypic, as well as phenotypic differences between young and old cells.

The Relationship Between Cellular Aging In Vitro and Cellular Aging In Vivo

Many of the morphological, physiological and biochemical characteristics that distinguish young from old cells in living mammals are exhibited by such cells when they are cultured in vitro. For example, fibroblasts of the dermal layer of skin and the connective tissue layer underlying the epithelia of the inner wall of the gastrointestinal tract display characteristics of aging similar to those found for fibroblasts in culture. Also, cells in vivo share many characteristics of cultured fibroblasts, including similar biochemical characteristics and tight control of growth, so that characteristics that distinguish young from old cells in culture are applicable to cells in living mammals.

A number of attributes have been identified that differentiate young and aged cells. In culture, young cells exhibit higher responsiveness to growth factors and higher rates of DNA and protein synthesis than old cells. Young mammalian, including human, fibroblast cells in tissue culture appear healthy and clean; possess a regular, long, thin spindle-shaped morphology; are tightly packed in arrays on becoming confluent on culture substrata; do not overgrow one another; seldom have other than one nucleus; and produce little debris in the culture medium. Fibroblast cells that are old display many age-related characteristics, including flattened and irregular morphology, abnormally large size, sparse growth, low cell yield per unit area of culture substratum, a significant frequency of polynucleated cells, difficulty in trypsinization, the inability to grow to confluence and a high rate of production of debris in the culture medium. The morphological characteristics that distinguish young from old cells, as well as the high level of autofluorescence found in old cells, reflect the various physiological and biochemical characteristics that distinguish young from aged cells.

The proliferative potential of normal human diploid cells is finite and a function of the number of cumulative population doublings (see, e.g., Hayflick et al. (1961) *Exp. Cell Res.* 25:585; and Hayflick (1985) *Exp. Cell Res.* 37:614). The lifetime of human cells under controlled conditions in vitro is reproducible, maximally about 45 to 60 cumulative population doublings for a primary culture, and is inversely proportional to the in vivo age of the donor from whom the cells were obtained (see, e.g., Martin et al. (1979) *Lab. Invest.* 23:86; Goldstein et al. (1969) *Proc. Natl. Acad. Sci. U.S.A.* 64:155; Schneider et al. (1976) *Proc. Natl. Acad. Sci. U.S.A.* 73:3584; and LeGuilty, et al. (1973) *Gereontologia* 19:303).

A measure of the "age" of fibroblasts in tissues of a living mammal, which normally divide periodically under tight growth control, is the number of cell divisions that have occurred between the cells and their predecessors at about the time of birth of the mammal. In cultures of normal fibroblasts, fibroblasts that have not been immortalized or transformed to a cancerous state, total proliferative capacity decreases as a function of the number of doublings that separates a culture from the primary culture from which it was derived. Because cell division occurs periodically and growth rate decreases rapidly as the finite life span of the cells is approached, there is typically a correlation between chronological age of the mammal and the age of particular cells measured by cell divisions between the cells and their predecessors at birth. The proliferative capacities of cells, such as fibroblasts in primary cultures established with normal dermal cells, are inversely related to donor age. Thus, fibroblasts in primary cultures established with normal cells from human adult dermis have a lower total proliferative capacity than fibroblasts in primary cultures established with normal cells from human fetal or newborn dermis.

The narrowly defined (within a few doublings) total proliferative capacity of normal fibroblasts, particularly of human origin, in culture is a manifestation of the tight proliferative control of such cells. This narrowly defined total proliferative capacity makes it possible to specify the total proliferative capacity of cells in vivo, such as fibroblasts of the dermis of the skin or the connective tissue layer underlying the intestinal epithelium, in living mammals in terms of a fixed number of doublings, limited to a narrow range characteristic of the species of the mammal (e.g., 45–60 for human fibroblast cells about 10 for murine fibroblast cells).

Under certain conditions cells that normally have a limited total proliferative capacity can be transformed to lose this limitation. Cultures of such cells can be passaged repeatedly without any apparent limit on number of passages; such cells are said to be immortalized. Immortalization is also a characteristic of cancer cells that, in addition to exhibiting little or no proliferative control, do not exhibit contact inhibition. The loss of limited total proliferative capacity characteristic of cells in culture that are transformed to the immortalized or cancerous state is often accompanied by an abnormally increased rate of proliferation or growth rate. Similarly, the loss of tight proliferative control that characterizes cancer cells in vivo is often accompanied by an abnormally increased growth rate of the cells.

Treatments that are designed to preserve the "young" phenotype of aging cells in vivo also invariably increase the growth rate of the treated cells. Treatments that artificially increase the rate of cell division or the total proliferative capacity of cells in culture beyond normal limits have been found to increase the risk of transformation to the immortalized or cancerous state. The risk of causing transformation by tampering with the tight proliferative control on cells, by tampering with growth rates and/or limits on total proliferative capacity, are presumably due to effects of such tampering on the gene expression. Further, treatments that increase growth rate or total proliferative capacity, such as epidermal and platelet-derived growth factors, insulin, glucocorticoids, extracts of Panax ginseng, and gibberellin plant hormones, are generally effective in preserving the young phenotype of only young cells, for which the treatments are needed least. Old cells that have proliferated at least about 80–90% of their normal life spans, respond little, if at all, to treatment with even much higher concentrations of these substances than those effective with younger cells.

Cellular Aging In Vivo

Skin, which is the external covering of the body, has two components: the epidermis that contains four layers and the dermis, also referred to as the corium, curls, derma, or true skin, that contains a superficial papillary layer and a deep reticular layer. Collagen constitutes about 80% of the dry weight of the dermis and is the major fibrillar component of human skin. The dermis is composed of connective tissue that contains lymphatics, nerves and nerve endings, blood vessels, sebaceous and sweat glands, and elastic fibers that provide the elastic properties of the skin. The mature fiber contains about 90% elastin and two glycosaminoglycans are present at concentrations of about 2% and 0.1%, respectively (see, e.g., Braverman (1982) *J. Invest. Dermatol.* 78:434–443). The coarse branching fibers are entwined with collagenous fiber bundles in the reticular dermis. The fibers rise from the deeper layers of the papillary layer of the dermis and, as they rise towards the epidermis, they split repeatedly become finer and form a network.

As humans age, there are changes in the quantity and integrity of dermal elastic tissue (Warren et al. (1991) *J. of the American Acad. Dermatology* 25:751–760). Gross alteration in elastin leads to alterations in the appearance of the skin (see, Bryce et al. (1988) *J. Invest. Dermatology* 91:175–180; Kornberg et al. (1985) *New Engl. J. Med.* 312:771–774; Shelley et al. (1977) *Br. J. Dermatol.* 7:441–445). The association of changes in the fibers and the appearance of wrinkles indicates a causal relationship between the integrity of the elastic fiber network and the mechanical properties of the skin. Aging skin is characterized by initial elastogenesis followed by a slow spontaneous progressive degradation of the elastic fibers that leads to laxity and wrinkling. Studies of skin from subjects of various ages indicate that the degradation of elastic fibers that begins about age 30 and becomes marked after age 70 is a major feature of aging skin.

In understanding the process of aging of human skin, it is pertinent to understand the role of fibroblasts, particularly in the dermis of human skin and in the corresponding connective tissue layer underlying the integuments of other mammals and the epithelia of the inner wall of the gastrointestinal tracts of humans and other animals. Fibroblasts synthesize components that are required for maintenance of the structural, functional and cosmetic integrity of the skin and the structural and functional integrity of other surface tissues covered by epithelia. These components include collagen and elastin, which are fibrous proteins responsible for the three-dimensional architecture of skin and the other surface tissues, fibronectin, which is a protein responsible for cell anchorage and maintenance of cell morphology; and a number of proteinaceous growth factors essential for the maintenance of epithelia and basal cell layers and connective tissue layers underlying them. Available evidence indicates that protein biosynthetic activity of fibroblasts decreases significantly with age. For example, the rate of collagen synthesis at about 70% of life expectancy for fetal-derived human fibroblasts in culture is only about 50% of that of such fibroblasts at less than 20% of life expectancy.

The changes in the appearance of the skin with age result from natural or intrinsic aging superimposed by actinic damage resulting from photoaging (see, e.g., Weiss et al. (1988) *J. American Medical Assoc.* 259:527–532). Intrinsic aging includes changes that occur as a result of endogenous factors and genetically programmed senescence, including epidermal and dermal atrophy. Photoaging results from long-term exposure to UV (ultra-violet) radiation, primarily from the sun. UV exposure is also associated with tumor induction and other skin pathologies. UV radiation from the sun includes UVB (280–315 nm) and the more penetrating UVA (315–400 nm) radiation. UVB causes erythema, skin cancer and dermal connective tissue damage. UVA also causes erythema and is carcinogenic at higher doses. Low doses (2.5 minimal erythemic doses (MEDs)) are sufficient to cause endothelial cell enlargement, extravasation of blood cells, and perivenular neutrophil infiltrates as wells increased concentrations of mediators of the inflammatory response (see, e.g., Kligman et al. (1985) *J. Invest. Dermatol.* 84:272-276).

Long-term UV exposure results in histological and visible changes in the skin, including: damage to the underlying connective tissue, manifested as elastosis and increases in the glycosaminoglycans and loss of collagen; dermal accumulation of elastin-staining material resulting from the degenerative changes in collagen fibers; epidermal dysplasia with cytologic atypia and loss of polarity of keratinocytes; and an inflammatory infiltrate (see, e.g., Bissett et al. (1987) *Photochemistry and Microbiology* 46:367-378). The degradation of elastic fibers and wrinkling associated with intrinsically aging skin also accompanies photoaging. In humans with advanced photodamage can be detected in the changes in the staining properties of dermal tissue resulting from changes in the insoluble and soluble fractions of collagen that occur as the entire upper dermis becomes filled with elastosis (Kligman et al. (1989) *J. Investigative Dermatol.* 93:210-214). The changes in collagen and elastic fiber over decades of such exposure result in skin that is wrinkled, yellowed, blotchy, lax, rough and leathery. Scanning electron microscopy of aged skin shows a more dense network of elastic fibers in a more disorganized arrangement than younger skin.

Exposure to sunlight is such a pronounced factor in premature aging that by middle age individuals who have been exposed to more sunlight appear older than those who have not. The extent of dermal degenerative change correlates with the visible signs of premature aging. The subepidermal band of normal dermis, which is a site of continual dermal repair, contains normal collagen fibers. This zone becomes visually evident, however, only after there is sufficient elastotic damage to delineate this region. The elastotic material is composed principally of elastin and microfibrillar proteins that codistribute with fibronectin (see, Schwartz (1988) *J. Invest. Dermatol.* 91:158-161). Actinic elastosis appears to be reversible to some extent by treatment with chemical peels, dermabrasion or topical application of tretinoin (see, e.g., Warren et al. (1991) *J. American Acad. Dermatol.* 25:751-760; and Weiss et al. (1988) *J. American Medical Assoc.* 259:527-532).

The Actinic Mouse as a Model for Aging Human Skin

The hairless mouse is a recognized model for studying aging human skin, including studying the effects of UV radiation on the aging process and on the development of pathologies of the skin (see, e.g., Kligman et al. (1985) in *Models in Dermatology*, Maibach et al. (eds.), Basel, Karger, pp. 59-68; Kligman et al. (1982) *J. Invest. Dermatol.* 78:181-189). UV-induced connective tissue changes is similar in humans and the hairless mouse. The action spectrum and time-course for UV-induced erythema in the hairless mouse and the human is similar to the sunburn response in man (Cole et al. (1983) *Photochem. Photobiol.* 37:623-631).

Chronic exposure of hairless mice to UV light in amounts sufficient to cause dermal elastosis and damage leads to wrinkles similar to wrinkles seen in human skin as a result of photoaging. In the hairless mouse, the wrinkles appear as regularly spaced furrows on the dorsal surface that do not disappear upon gentle stretching. The wrinkles form when the underlying muscle contracts and the skin adapts by forming folds pedicular to the line of the contraction (Wright et al. (1973) *J. Soc. Cosmet. Chem.* 24:81-85). These are comparable to so-called permanent deep wrinkles that appear on sun-exposed human skin that age more rapidly than areas of the body that are not exposed.

Studies using hairless mice demonstrate that the visible appearance of the skin changes with UV exposure and that the changes mirror those seen in human skin after long-term UV exposure. As with human skin, the changes, which are manifested as wrinkling, sagging and tumor development, are a function of the quantity and quality of UV exposure. Studies using these mice have shown that skin wrinkling is induced by UVB and UVB plus UVA (315-400 nm); skin sagging is induced by high doses of UVA; tumors develop upon exposure to UVB and UVB plus UVA irradiation (see, e.g., Bissett et al. (1989) *Photochem. Photobiol.* 50:763-769). Exposure of the mice to UVB+UVA exposure results in thickened epidermis and changes in several components of the dermis, including thickening and proliferation throughout the upper dermis of the elastic fibers and hyperproliferation of fibroblasts and sebaceous cells and the formation of dermal cysts from remnants of follicular epithelium. The action spectrum for thickening and glycosaminoglycan increase also appears to be in the UVB range of between 285-300 nm. Ultimately, after long-term exposure (about 16 weeks), the skin becomes elastotic with thick, tangled masses of elastic fibers in the dermis. The entire dermis exhibits an increase in cellularity and an infiltrate of inflammatory cells, primarily macrophages and a few neutrophils (Bissett et al. (1987) *Photochemistry and Photobiology* 46:367-378).

The hairless mouse also serves as a model for testing potential treatments that reverse or repair UV-induced damage and changes associated with aging per se. Studies, using hairless mouse models, indicate that upon cessation of the UV irradiation, a band of new dermal tissue is produced in the immediate subepidermal region, which compresses the old elastotic tissue. The width of this band serves as a measure of the repair. Retinoid treatment causes dose-dependent increments in the area of the dermal repair zone. For example, topical application of all-trans retinoic acid for 10 weeks stimulates the deposition of a 100 μ deep subepidermal band of collagen in photoaged hairless mice (Schwartz et al. (1991) *J. Invest. Dermatol* 96:975-978). The resulting reconstructed dermis is thickened, contains new collagen, and the tangled, disorganized elastin, produced upon exposure to the UV irradiation, is packed into a thin layer in the lower dermis, thereby eliminating the "permanent wrinkle" on the surface.

Cytokinins

There have been a few reports suggesting the use of kinetin, a cytokinin, to promote cell division of mammalian cells and on this basis suggest its use in cosmetics. Such reports describe the use of kinetin in conjunction with other cell growth- or cell division-promoting compounds and postulate activity based on the cell division-promoting activity of kinetin. For example, French Patent 1,587,633 (27 Mar. 1970) describes a method for preparing a plant extract that is enriched in kinetin. This French Patent suggests that, because the rate of cell renewal diminishes with age, the plant extract may be used in a cosmetic formulation for the treatment of sagging skin and wrinkles by increasing the rate of cell proliferation. Japanese patent Application Publication No. 60-19709 (1985) describes a composition that contains no more than 1% of kinetin and no more than 20% of an uncharacterized lithosperum root extract and is said to accelerate cell division in human skin and thereby prevent skin-aging.

The cytokinins are a class of plant hormones defined by their ability to promote cell division in plant tissue explants in the presence of an auxin, such as indoleacetic acid, and nutrients, including vitamins, mineral salts, and sugar. In promoting cell division of plant cells, cytokinins are active at low concentrations (as low 0.01 parts per million (ppm)), but exhibit activity only in the presence of an auxin. Certain cytokinins, including zeatin (6-(3-hydroxymethyl-3-methylallyl)-aminopurine) and 6-(3,3-dimethylallyl)aminopurine, also occur as the base moiety components of transfer RNA in yeast, bacterial, animal cells and plant cells. The cytokinin kinetin (6-furfuryl-aminopurine) forms complexes with certain RNA-binding proteins of wheat embryo extracts and appears to promote protein synthesis in plants (see, e.g., Spirin and Ajtkhozhin (1985) Trends in Biochem. Sci., p. 162). Kinetin and other cytokinins are used in conjunction with auxin used in horticulture and in plant tissue culture, such as in the production of plantlets from plant callus tissue. Cytokinins are also used in the production of protein-rich yeast (see e.g., East German Patent No. 148,889 (1981) (Derwent World Patent Index Abstract)) and to augment the growth of microbial cultures (Merck Index, 10th Ed. (1983) Entry 5148, Merck and Co., Rahway, N.J., U.S.A.).

Certain cytokinins have been shown to inhibit the growth of tumor cells in vitro (see, e.g., Katsaros et al. (1987) FEBS Lttrs. 223: 97–103). It appears that this effect is mediated via the cytotoxic affects of adenosine analogs, such as the 6-(substituted amino) purine cytokinins, that interfere with tRNA methylating enzymes (Wainfan et al. (1973) Biochem. Pharmacol. 22:493–500). When immortalized fibroblast cells are contacted with adenosine analogs the cultured cells exhibit decreased growth rate and a change in morphology from the normal flattened elongated morphology typical of cultured fibroblasts to a very elongated spindle-shape characteristic of a cytotoxic response. The very elongated shape of immortalized cells exhibiting this response is not shape characteristic of young, healthy, primary cultures of normal diploid fibroblasts.

Reversing, Slowing or Ameliorating the Adverse Effects of Cellular Aging

Preventing, reversing or slowing the process of cellular aging has been a persistent, though elusive, goal of biological science, that would have a number of significant and practical consequences. Preventing the aging of cells in human skin or other organs would be associated with preservation of structural and functional integrity and also cosmetic integrity. If cultured cells could be treated so that they retain characteristics of young cells, the production of valuable products by such cells in culture could be improved.

Any composition intended for use to reverse, slow, or otherwise ameliorate the adverse effects of aging that is used to treat cells in vivo or in culture that acts by increasing growth rate or total proliferative capacity of cells, however, must be viewed with caution. Since tissues, including the skin and intestinal wall, contain cells normally under tight proliferative control, any treatment to ameliorate the adverse effects of aging on cells by increasing the rate of cell division or total proliferative capacity of the cells has the potential to promote undesirable transformation of the treated cells. Thus, it is undesirable for cosmetics or pharmaceuticals intended for the treatment of humans to promote cell division, since promoting increased cell division may result in a loss of the tight proliferative control and lead to pre-cancerous or cancerous transformation of the treated cells. In addition, promoting cell division may also lead to cosmetically unacceptable changes in treated cells and tissues, such as thickening of the treated tissues.

Compositions and methods that ameliorate the adverse effects of aging on morphological, physiological, and biochemical characteristics of cells but that do not lead to potentially harmful increases in the growth rate or total proliferative capacity of the treated cells would be advantageous. Such compositions or methods are not, however, available. Also, because of the important role of protein synthesis by fibroblasts in maintaining the health of skin and other surface tissues, and because available evidence indicates that protein biosynthetic activity of fibroblasts decreases significantly with age, methods and compositions that alter the biosynthetic activity of fibroblasts in vivo, without affecting the total proliferative capacity of growth rate of such fibroblasts, would be especially advantageous.

Therefore, it is an object herein to provide compositions and methods for ameliorating the adverse effects of aging on mammalian cells in vitro and in vivo without substantially altering the growth rate or total proliferative capacity of the treated cells. In particular, it is an object herein to provide compositions and methods for reducing or reversing the wrinkling and sagging and other characteristics associated with aging human skin. It is also an object herein to provide compositions and methods for ameliorating the adverse effects of aging on cultured cells.

SUMMARY OF THE INVENTION

Compositions containing effective concentrations of one or more 6-(substituted amino)purine cytokinins are provided. Preferred 6-(substituted amino)purine cytokinins are kinetin and 6-amino purine analogs thereof of Formula I:

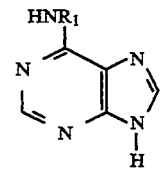

in which $R_1$ is furfuryl, phenyl, benzyl, alkyl of 4, 5 or 6 carbons, branched alkyl of 4, 5 or 6 carbons, (cyclohexyl)methyl ($-CH_2(C_6H_{11})$), 3,3-dimethylallyl ($-CH_2CH=C(CH_3)_2$) or 3-hydroxymethyl-3-methylallyl

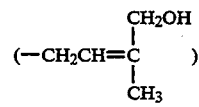

are provided. Preferred compounds of formula I, include, but are not limited to, kinetin, zeatin, benzyl adenine and isopentenyl adenine. The concentrations of the compounds in the compositions are effective for reversing or decreasing, or ameliorating, UV damage or other age-associated changes that occur in human skin in vivo and for reversing, decreasing or ameliorating the morphological and other phenotypic changes that cells cultured in vitro exhibit as a function of the number of cell doublings, without, either in vivo or in vitro, substantially or detectably altering the total proliferative capacity or growth rate of the treated cells.

The compositions and methods are provided for ameliorating, including reversing or slowing, the adverse effects of aging on mammalian cells, including such cells in culture and in vivo, such as in human skin. The compositions and methods, among other applications, are useful for slowing and reversing the degeneration of the structural, functional and cosmetic integrity of human skin that normally accompanies aging. The compositions and methods are also effective for improving the production of useful products, such as proteins, from cell cultures.

In particular, cosmetic and pharmaceutical compositions and tissue culture medium containing effective concentrations of one or more of the 6-(substituted amino)purine cytokinins and/or cosmetically or pharmaceutically acceptable derivatives of the 6-(substituted amino)purine cytokinins, including prodrugs, effective for ameliorating the adverse effects of aging of human skin and other tissues in vivo or tissue culture cells in vitro are provided.

In preferred embodiments, the cosmetic and pharmaceutical compositions are formulated for topical, local, or oral application. In more preferred embodiments, the compositions are formulated for topical application to human skin and the ameliorative effects are manifested as a decrease in the number or depth of wrinkles, a delay in the appearance of such wrinkles, or a decrease or delay in the development of loose sagging skin or other characteristics, such as discoloration, that are associated with aging skin. These effects include any other cosmetic changes that are recognized as accompanying aging skin.

In other preferred embodiments, the compositions do not contain any ingredients, such as auxin or other plant or mammalian growth factors, that, when used in conjunction with the 6-(substituted amino) purine cytokinin, substantially alter, particularly increase, the growth rate or total proliferative capacity of the treated cells.

Methods for ameliorating the adverse effects of aging on mammalian cells in which cells are contacted with a composition containing an effective amount to ameliorate the adverse effects on such cells of a cytokinin, which is a 6-(substituted amino)purine are provided. The methods provide a means for maintaining cells in culture or in vivo in a younger stage of growth by delaying the onset of the undesirable morphologic and phenotypic characteristics associated with aging, but without increasing the total proliferative capacity or growth rate of such cells, and, thus, without the risking the transformation of such cells to cancerous cells.

In practicing the methods, mammalian cells are contacted with the compositions that contain effective concentrations of one or more of the 6-(substituted amino)-purine cytokinins in order to ameliorate the adverse effects of aging on such cells by delaying, and even reversing, the onset of age-related morphological changes that normally occur with aging of the cells without increasing the growth rate or total proliferative capacity of the cells are provided. The mammalian cells that can be treated with the methods and compositions, include, but are not limited to, human cells, and cells in culture as well as cells in vivo in living mammals. In preferred embodiments, human skin is treated by topical application of the compositions in order to reverse, slow or lessening the cosmetic changes in the skin, particularly wrinkling, associated with aging.

Thus, the methods, and compositions for practicing the methods, for slowing (or reversing) the degeneration, which normally accompanies aging, of the structural and functional integrity of skin and epithelia of the inner wall of the gastrointestinal tract and the cosmetic integrity of skin or for retaining younger productive characteristics of cells in vitro do not significantly affect either the growth rate or the total proliferative capacity of cells treated according to the methods. The compositions and methods do not affect the rate or amount of DNA synthesis in treated cells nor the tight proliferative control under which many cells, in vivo, such as fibroblasts and certain cells of the epidermis and other epithelia, must remain to function normally.

DETAILED DESCRIPTION OF THE INVENTION

Definitions

Unless defined otherwise, all technical and scientific terms used herein have the same meaning as is commonly understood by one of skill in the art to which this invention belongs. All patents and publications referred to herein are incorporated by reference herein.

As used herein, "ameliorating the adverse effect of aging" of mammalian cells means that the development of the morphological changes, described earlier, that normally occur with "aging" in normal mammalian cells in culture or in vivo is slowed, reversed or delayed. The adverse effects of aging also include age related changes in gene expression and protein biosynthesis. The ameliorative effect referred to herein is achieved without increasing the growth rate or total proliferative capacity of the cells that are treated.

Ameliorating the adverse effects of aging on cells, including the effects on in vitro cultured cells and in vivo cells, is detected as a delay or reversal of the onset of age-related morphological and phenotypical changes that normally occur with aging of the cells. These changes include the changes detected in tissue culture cells, such as the failure of older cells to respond to exogenous growth factors and the high level of autofluorescence found in old cells. As cells age they exhibit an age-dependent loss of proliferative potential. Cultured fibroblast cells that are old display many age-related characteristics, including flattened and irregular morphology, abnormally large size, sparse growth, low cell yield per unit area of culture substratum, a significant frequency of polynucleated cells, difficulty in trypsinization, the inability to grow to confluence and a high rate of production of debris in the culture medium. Young cells exhibit higher responsiveness to growth factors and higher rates of DNA and protein synthesis than old cells. Young mammalian, including human, fibroblast cells in tissue culture appear healthy and clean; possess a regular, long, thin spindle-shaped morphology; are tightly packed in arrays on becoming confluent on culture substrata; do not overgrow one another; seldom have other than one nucleus; and produce little debris in the culture medium. Age related changes in vivo include changes in mammalian tissues, such as the development of wrinkles, lines, sagging skin, discolorations, leathery, yellowed appearance associated with the cosmetic appearance of the skin as well as the associated changes in the structural and functional integrity of the tissue.

As used herein, the "total proliferative capacity" of normal cells, such as fibroblast cells, is a measure of the finite proliferative capacity of cells and refers to the total number of doublings of cell number that a culture of such cells can undergo before growth of the culture ceases and is a function of the age of the donor from which the cells were obtained. Cells obtained from fetal tissue exhibit a greater proliferative capacity in culture than cells obtained from adult tissue.

As used herein, the "life expectancy" or "normal life span" of normal cells is the "total proliferative capacity" of the primary culture from which the culture in which the cells occur was derived.

As used herein, reference to the phenotypic characteristics of "young" cells refers to cells that have proliferated for less about half of their life spans; and reference to the phenotypic characteristics of "old" cells, refers to those that have proliferated for at least about 75% of their normal life span.

As used herein, "growth rate" or "rate of proliferation" is a measure of the rate at which cells divide. One unit of measure recognized by those of skill in the art is the reciprocal of doubling time. At the end of the life span of a culture of normal cells, the cessation of culture growth appears very quickly, decreasing from near normal values characteristic of young cells to zero in only a few doublings.

As used herein a prodrug is a compound that, upon in vivo administration, is metabolized or otherwise converted to the biologically, pharmaceutically or therapeutically active form of the compound.

As used herein, substantially altering the growth rate or total proliferative capacity means to change beyond the amount that is within normal variation among cells and tissues the rate of cell division or the number of cell doublings. In particular, the growth rate or total proliferative capacity is not altered such that the treated cells are immortalized or undergo malignant transformation. In the case of treated in vivo treated cells, the treated tissue does not substantially change size, thickness or develop precancerous or cancerous cells. Methods for assessing the growth rate and total proliferative capacity are known to those of skill in the art. Any such method, including those exemplified herein, may be used to assess the alteration in growth rate or total proliferative capacity.

Compositions and Methods for Ameliorating the Adverse Effects of Aging

Compositions for ameliorating the adverse effects of aging on mammalian cells, containing, at a concentration which is effective to ameliorate said adverse effects on such cells, one or more 6-(substituted amino)purine cytokinins of formula I:

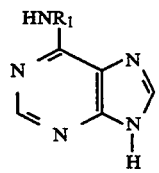

in which $R_1$ is furfuryl, phenyl, benzyl, n-alkyl of 4, 5 or 6 carbons, branched alkyl of 4, 5 or 6 carbons, (cyclohexyl)methyl, 3,3-dimethylallyl, or 3-hydroxymethyl-3-methylallyl are provided. Among the 6-(substituted amino)purine cytokinins that are intended to be used, singly or in combination, as the adverse-age-effect-ameliorating-effective compound in the methods and compositions herein are kinetin, zeatin, benzyl adenine, isopentenyl adenine, (6-(3-hydroxymethyl-3-methylallyl)-aminopurine), 6-(3,3-dimethylallyl)aminopurine, 6-(benzyl)aminopurine, 6-(phenyl)aminopurine, 6-(n-alkyl)aminopurine, in which the n-alkyl group has 4, 5 or 6 carbons, and 6-(cyclohexyl)methylaminopurine. Most preferred is kinetin (6-(furfuryl)aminopurine). Other such 6-(substituted amino) purine cytokinins compounds that, in conjunction with auxin, promote cell division in plant tissue culture cells, may be tested for the ability to ameliorate the adverse effects of aging on mammalian cells in vitro and in vivo. Those compounds that slow, reverse or ameliorate the adverse effects of aging but do not substantially alter the growth rate or total proliferative capacity of the treated cells are selected and formulated as cosmetics, pharmaceutics or added to tissue culture medium at effective concentrations. Such concentrations are preferably about 0.1 ppm to about 250 ppm, preferably 10 ppm to about 100 ppm, in tissue culture medium and about 50 ppm to about 5,000 ppm, preferably about 100 to about 1,000 ppm, in cosmetic and pharmaceutical compositions. The precise concentrations, particularly for in vivo use, may be determined empirically and may be higher, particularly for in vivo use, depending upon the ability of the carrier or vehicle to deliver the compound or compounds to the treated cells or tissue and the manner in which compositions is contacted with the treated cells or tissue.

The pharmaceutical and cosmetic compositions herein include one or more of the compounds of formula I at a concentration effective for ameliorating the adverse effects of aging without substantially altering the growth rate or total proliferative capacity of cells and may include effective concentrations of other age-ameliorative ingredients, such as one or more retinoids, including as all-trans retinoic acid, at concentrations, typically about 0.5–1%, effective for treating skin for acne. It is understood, however, that such additional ingredients do not potentiate or induce any cell proliferation or cell division promoting activities of the 6-(substituted amino)purine cytokinin. In particular, the compositions herein do not include auxins, which are required for the cell-division promoting activity of cytokinins in plants.

The cells, if in culture, can be derived from any tissue and, in vivo, can be part of any tissue. The methods and compositions are preferably applied to tissues in vivo in humans that include fibroblasts, such as the dermis of human skin and the connective tissue layer underlying the epithelium of the inner wall of the human small intestine or stomach. The most preferred application is to human skin.

The skilled artisan can ascertain whether a composition, to which mammalian cells are exposed, includes an amount of a 6-(substituted amino)purine cytokinin that is effective to ameliorate the adverse effects of aging on the cells. Morphological changes associated with aging are discerned by the skilled by microscopic examination of cells, removed from a culture, taken by biopsy from tissue, or tested using other standard methods for assessing the effects of treatments on human skin and other tissues (see, e.g., Warren et al. (1991) *J. Amer. Acad. Dermatol.* 25:751-760 Kligman et al. (1985) *Plast. Reconstr. Surg.* 75:653-659; and Stegman (1982) *Aesthet. Plast. Surg.* 6:123-135). In addition, in vivo testing on model animal systems, such as hairless mice (see, e.g., Schwartz et al. (1991) *J. Invest. Dermatol.* 96:975-978; Kligman et al. (1985) in *Models in Dermatology*, Maibach et al. (eds.), Basel, Karger, pp. 59-68; Kligman et al. (1982) *J. Invest. Dermatol.* 78:181-189; and Cole et al. (1983) *Photochem. Photobiol.* 37:623-631), from which in vivo human effectiveness and effective doses may be ascertained, may be used. In vitro tests, such as those exemplified herein, to ascertain the effects on the total proliferative capacity and growth rates of cells may be used.

Treatment of Tissue Culture Cells

The methods and compositions for use in vitro are effective at concentrations of the 6-(substituted amino)-purine cytokinin typically in the range of between about 0.1 ppm to about 100 ppm. When kinetin is used the preferred concentration range is about $10^{-6}$ M and $5 \times 10^{-4}$ M in a tissue culture medium. The compositions may be formulated in numerous forms, depending on the nature and the surroundings of the cells to which adverse-age-effect-ameliorative amounts of 6-(substituted amino)purine cytokinins are to be applied. At these concentrations, the cytokinin apparently has no toxic effect on mammalian cells.

In the case of mammalian cells in culture, which may be grown directly from tissue without genetic engineering or may be genetically modified to produce a desired product by any of various known genetic engineering techniques, and which, as understood in the art, can be used to make valuable proteins, such as lymphokines or hormones, for diagnostic, therapeutic or other applications, ameliorating the adverse effects of aging with the methods of compositions advantageously maintains the rate of protein synthesis of such cells at a level characteristic of cells "younger" than the cells actually are. Addition of an effective amount of a 6-(substituted amino)purine cytokinin to a culture medium of mammalian cells, that have been passaged numerous times and that have a rate of protein synthesis and morphological and phenotypic characteristics of aging cells, reverses morphological and phenotypic characteristics to those characteristic for younger cells and may alter the rate, quantity or quality of protein synthesis so that the amount of collagen or other such proteins required for structural and functional integrity of the treated cells is increased.

The cells in culture are bathed, suspended or grown in a culture medium used for mammalian cells. The medium contains an effective concentration one or more 6-(substituted amino)purine cytokinins of formula I:

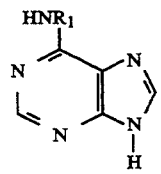

in which $R_1$ is furfuryl, phenyl, benzyl, n-alkyl of 4, 5 or 6 carbons, branched alkyl of 4, 5 or 6 carbons, (cyclohexyl)methyl, 3-hydroxymethyl-3-methylallyl or 3,3-dimethylallyl. Preferred compounds of formula I, include, but are not limited to, kinetin, zeatin, benzyl adenine and isopentenyl adenine. The preferred concentration of the compounds of formula I in the medium is about 0.1 and about 500 ppm, generally about 0.1 to 100 ppm, or a concentration of equivalent activity to a kinetin concentration of between about $10^{-6}$ M (1 μM or about 5 ppm) to about $5 \times 10^{-4}$ M (50 μm or about 250 ppm) For the most preferred cytokinin, kinetin, the preferred concentration range is about 25 μM to about 250 μM or about 5 ppm to about 50 ppm in the culture medium.

It is understood that the precise concentration for each compound of formula I or mixture thereof may be empirically determined by testing a range of concentration and selecting those in which the adverse effects of aging, as manifested by morphological changes or other suitable age-related markers, are reduced, slowed, reversed, or otherwise ameliorated, but the growth rate or proliferative capacity of the cells is not substantially altered so that the cells become immortalized or transformed.

Cultured diploid fibroblast cells were cultured in the presence of kinetin, and the growth rate and proliferative capacity of the cells was tested by nuclear track autoradiography and $^3$H-thymidine-uptake in acid-insoluble material in order to assess the effects of cytokinins on DNA synthesis in mammalian cells and the risk that such cells, in the presence of cytokinins, would be transformed to the cancerous state. Treatment with kinetin did not appear to alter the rate or amount of DNA synthesis in cultured fibroblasts.

Formulation of Compositions for In Vivo Use

Effective concentrations of one or more of the 6-(substituted amino)purine cytokinin, preferably those of formula I, or cosmetically or pharmaceutically acceptable derivatives thereof are mixed with a suitable cosmetic or pharmaceutical carrier or vehicle. The resulting mixture may be a solution, suspension, emulsion or the like. The 6-(substituted amino)purine cytokinin may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the adverse effects of aging on the treated cells and tissue may be empirically determined, but generally are in the range of about 50 ppm to about 5,000 ppm, and typically 100 ppm and 1,000 ppm.

The active compounds can be administered by any appropriate route, for example, orally or topically, in liquid, semi-liquid or solid form and are formulated in a manner suitable for each route of administration. Preferred modes of administration include topical application to the skin and oral administration to the dermis of the skin of the connective tissue layer underlying the epithelia of the inner wall of the gastrointestinal tract and stomach.

Cosmetic and pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including tissue culture and hairless mice or other suitable animal model.

The concentration of active compound in the composition will depend on absorption, inactivation, excretion rates of the active compound, the dosage schedule, and amount administered as well as other factors known to those of skill in the art. Typically a therapeutically effective dosage should deliver a concentration of at least about 10 ppm up to about 5,000 ppm, preferably 50 ppm to about 1,000 ppm, of the active compound to the treated tissue. The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Formulation of Cosmetic and Pharmaceutical Compositions for Treatment of the Skin For treatment of the skin, the compounds may be formulated as cosmetic or pharmaceutical compositions for local or topical application to the skin in which the 6-(substituted amino)purine cytokinin(s) is mixed with a pharmaceutically or cosmetically acceptable carrier. The compositions may be provided in the form of gels, creams, lotions, solids, solutions or suspensions, or aerosols. Compositions for treating human skin are formulated for topical application with a 6-(substituted amino)purine cytokinin, preferably one of those of the above-defined Formula I, in an effective concentration range, between about 0.1 ppm and about 5,000 ppm, preferably, about 50 ppm to about 5,000 ppm, more preferably, about 100 ppm to about 1,000 ppm in a cream, ointment, lotion, gel, solution or solid base or vehicle known in the art to be non-toxic and dermatologically acceptable. The concentration or weight fraction of 6-(substituted amino)purine cytokinin dissolved, suspended, dispersed, or otherwise mixed in a composition for use with human skin will be such that the 6-(substituted amino)purine cytokinin is delivered at an effective concentration, generally between at least about 0.2 ppm and about 5,000 ppm to active cells of the skin, such as fibroblasts, such that the adverse effects of aging are reduced, reversed or delayed, and such that the rate of cell division or total proliferative capacity of the cells is not substantially altered, particularly such that the treated cells or tissues do not exhibit any signs typical of cancerous or pre-cancerous alterations or any other cosmetically undesirable changes, such as the development of lesions. Generally, emollient or lubricating vehicles that help hydrate the skin are more preferred than volatile vehicles, such as ethanol, that dry the skin.

Examples of suitable bases or vehicles for preparing compositions for use with human skin are petrolatum, petrolatum plus volatile silicones, lanolin, cold cream (USP), and hydrophilic ointment (USP). Compositions contain between about 10 ppm and about 5,000 ppm, and preferably deliver at least about 100 ppm to about 1,000 ppm of one or more 6-substituted cytokinins formulated for topical application, such as emulsified, suspended or otherwise mixed with a suitable ointment or cream base.

The choice of an acceptable vehicle is largely determined by the way the 6-(substituted amino)purine cytokinin is to be administered. Such methods include topical administration. Suitable pharmaceutically and dermatologically acceptable vehicles for topical application include those suited for use in lotions, creams, solutions, gels, tapes and the like. Generally, the vehicle is either organic in nature or an aqueous emulsion and capable of having the 6-(substituted amino)purine cytokinin dispersed, suspended or dissolved therein. The vehicle may include pharmaceutically-acceptable emollients, skin penetration enhancers, coloring agents, fragrances, emulsifiers, thickening agents, and solvents. A more detailed description of such forms follows:

Formulation of Cosmetic Compositions

1. Lotions

The lotions contain an effective concentration of one or more 6-(substituted amino)purine cytokinins. The effective concentration is preferably effective to deliver the 6-(substituted amino)purine cytokinin(s) at a concentration of between about 0.2-10 ppm to about 1,000 ppm up to about 5,000 ppm to active cells of the skin, particularly the fibroblasts in the dermis. The lotions also contain from 1% to 50%, preferably from 3% to 15%, of an emollient and the balance water, a suitable buffer, a $C_2$ or $C_3$ alcohol, or a mixture of water or the buffer and the alcohol. Any emollients known to those of skill in the art as suitable for application to human skin may be used. These include, but are not limited to, the following:

a. Hydrocarbon oils and waxes, including mineral oil, petrolatum, paraffin, ceresin, ozokerite, microcrystalline wax, polyethylene, and perhydrosqualene.

b. Silicone oils, including dimethylpolysiloxanes, methylphenylpolysiloxanes, water-soluble and alcohol-soluble silicone-glycol copolymers.

c. Triglyceride fats and oils, including those derived from vegetable, animal and marine sources. Examples include (but are not limited to) castor oil, safflower oil, cotton seed oil, corn oil, olive oil, cod liver oil, almond oil, avocado oil, palm oil, sesame oil, and soybean oil.

d. Acetoglyceride esters, such as acetylated monoglycerides.

e. Ethoxylated glycerides, such as ethoxylated glyceryl monstearate.

f. Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmirate, isopropyl palmirate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

g. Alkenyl esters of fatty acids having 10 to 20 carbon atoms. Examples thereof include (but are not limited to) oleyl myristate, oleyl stearate, and oleyl oleate.

h. Fatty acids having 9 to 22 carbon atoms. Suitable examples include (but are not limited to) pelargonic, lauric, myristic, palmitic, stearic, isostearic, hydroxystearic, oleic, linoleic, ricinoleic, arachidonic, behenic, and erucic acids.

i. Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols.

j. Fatty alcohol ethers, including, but not limited to ethoxylated fatty alcohols of 10 to 20 carbon atoms, such as (but are not limited to) the lauryl, cetyl, stearyl, isostearyl, oleyl, and cholesterol alcohols having attached thereto from 1 to 50 ethylene oxide groups or 1 to 50 propylene oxide groups or mixtures thereof.

k. Ether-esters, such as fatty acid esters of ethoxylated fatty alcohols.

l. Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

m. Polyhydric alcohols and polyether derivatives, including, but not limited to, propylene glycol, dipropylene glycol, polypropylene glycol (M.W. 2,000–4,000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6,000), methoxy polyethylene glycols 350, 550, 750, 2,000, 5,000, poly[ethylene oxide] homopolymers (M.W. 100,000–5,000,000), polyalkylene glycols and derivatives, hexylene glycol (2-methyl-2,4-pentanediol), 1,3-butylene glycol, 1,2,6,-hexanetriol, ehtohexadiol USP (2-ethyl-1,3-hexanediol), $C_{15}$–$C_{18}$ vicinal glycol and polyoxypropylene derivatives of trimethylolpropane.

n. Polyhydric alcohol esters, including, but not limited to, ethylene glycol mono- and di-fatty acid esters, diethylene glycol mono- and di-fatty acid esters, polyethylene glycol (M.W. 200–6,000), mono- and di-fatty esters, propylene glycol mono- and di-fatty acid esters, polypropylene glycol 2,000 monooleate, polypropylene glycol 2,000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

o. Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

p. Vegetable waxes, including (but not limited to) carnauba and candelilla waxes.

q. Phospholipids, such as lecithin and derivatives.

r. Sterols, including, but not limited to, cholesterol and cholesterol fatty acid esters.

s. Amides, such as fatty acid amides, ethoxylated fatty acid amides, and solid fatty acid alkanolamides.

The lotions further preferably contain from 1% to 10%, more preferably from 2% to 5%, of an emulsifier. The emulsifiers can be nonionic, anionic or cationic. Examples of satisfactory nonionic emulsifiers include (but are not limited to) fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6,000, propylene glycols of molecular weight 200 to 3,000, glycerol, sorbitol, sorbitan, polyoxyethylene sorbitol, polyoxyethylene sorbitan and hydrophilic wax esters. Suitable anionic emulsifiers include (but are not limited to) the fatty acid soaps, e.g. sodium, potassium and triethanolamine soaps, wherein the fatty acid moiety contains from 10 to 20 carbon atoms. Other suitable anionic emulsifiers include (but are not limited to) the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the 6-(substituted amino)purine cytokinin is dissolved, suspended or otherwise uniformly dispersed in the mixture.

Other conventional components of such lotions may be included. One such additive is a thickening agent at a level from 1% to 10% of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

2. Creams

The creams are formulated to contain an effective concentration of one or more 6-(substituted amino)purine cytokinins. The effective concentration is typically an amount effective to deliver the 6-(substituted amino)-purine cytokinin(s) to the treated tissue at between about 0.1 ppm and about 1,000 ppm up to about 5,000 ppm to active cells of the skin, particularly the fibroblasts in the dermis. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included is in the composition at a level from 3% to 50%, preferably from 5% to 20%.

3. Solutions and Suspension

The solutions are formulated to contain an effective amount of one or more 6-(substituted amino)purine cytokinin(s), which is typically an amount effective to deliver the 6-(substituted amino)purine cytokinin(s) at between about 0.1 ppm and about 1,000 ppm up to about 5,000 ppm to active cells of the skin, particularly the fibroblasts of the dermis; the balance is water, a suitable organic solvent or other suitable solvent or buffer. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions that are formulated as solutions or suspensions may be applied to the skin, or, may be formulated as an aerosol and applied to the skin as a spray-on. The aerosol compositions further contain from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

4. Gels

Gel compositions can be formulated by simply admixing a suitable thickening agent to the previously described solution or suspension compositions. Examples of suitable thickening agents have been previously described with respect to the lotions.

The gelled compositions contain an effective amount of one or more 6-(substituted amino(purine cytokinins, which is typically an amount effective to deliver the 6-(substituted amino)purine cytokinin at between about 0.1 ppm and about 1,000 ppm up to about 5,000 ppm to active cells of the skin, particularly the fibroblasts of the dermis; from 5% to 75%, preferably from 10% to 50%, of an organic solvent as previously described; from 0.5 % to 20%, preferably from 1% to 10% of the thickening agent; the balance being water or other aqueous carrier.

5. Solids

Compositions of solid forms may be formulated as stick-type compositions intended for application to the lips or other parts of the body. Such compositions contain an effective amount of one or more 6-(substituted amino)purine cytokinins. The amount is typically an amount effective to deliver the 6-(substituted amino)purine cytokinin(s) at between about 0.1 ppm and about 1,000 ppm up to about 5,000 ppm to active cells of the skin, particularly the fibroblasts of the dermis. The solids also contain from 50% to 98%, preferably from about 60% to 90%, of the previously described emollients. This composition can further contain from 1% to 20%, preferably from 5% to 15%, of a suitable thickening agent, and, if desired or needed, emulsifiers and water or buffers. Thickening agents previously described with respect to lotions are suitably employed in the compositions in solid form.

An example of a composition suitable for application to human facial skin contains at least 10 ppm to 100 ppm, preferably up to 1,000–5,000 ppm of kinetin in a base prepared by mixing (by weight) 10 parts glycerol monostearate, 10 parts cetyl alcohol, 30 parts spermaceti, 10 parts Tween 20 (polyoxyalkylene derivative of sorbitan monostearate), 10 parts Span 20 monolaurate), 12.5 parts glycerin, and 100 parts water. Kinetin may also be used with or substituted by one or more other 6-(substituted amino) purine cytokinins, including zeatin, 6-(3,3-dimethylallyl)aminopurine, 6-benzylaminopurine, and a combination of kinetin and 6-(n-hexyl)aminopurine or 6-benzylaminopurine, that exhibit adverse-age-effect-ameliorative activity but do not substantially alter the growth rate or proliferative capacity of the treated cells, particularly to avoid immortalizing or transforming the treated cells.

Other ingredients, such as preservatives, including methyl-paraben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

A composition may also include adverse-age-effect-ameliorative active ingredients, such as retinoids, other than 6-(substituted amino)purine cytokinins, but should not include ingredients, such as auxin, that potentiate the cell-division inducing properties of kinetin. One advantage of employing such cytokinins alone, however, is that the growth rate and total proliferative capacity of treated cells are not substantially or significantly affected. This advantage will tend to be diluted if other such ingredients that increase growth rate, total proliferative capacity, or both, of treated cells are added to the compositions. Consequently, preferred compositions contain, as the only adverse-age-effect-ameliorative ingredient, one or more 6-(substituted amino)purine cytokinin.

Formulation of Compositions for Treatment of the Connective Tissue Layer Underlying the Epithelia of the Gastrointestinal Tract For treatment of the connective tissue layer underlying the epithelia of the inner wall of the gastrointestinal tract, oral administration is preferred. For oral administration, the compound or compounds may be provided in a composition that protects it from the acidic environment of the stomach. For example, the composition can be formulated in an enteric coating that maintains its integrity in the stomach and releases the active compound in as it passes through the gastrointestinal tract. The composition may also be formulated in combination with an antacid or other such ingredient.

Oral compositions will generally include an inert diluent or an edible carrier and may be provided as a liquid suspension or solution or compressed into tablets or enclosed in gelatin capsules. For the purpose of oral therapeutic administration, the active compound or compounds can be incorporated with excipients and used in the form of solutions or suspensions, tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors. The active materials can also be mixed with other active materials which do not impair the desired action, or with materials that supplement the desired action.

Solutions or suspensions used for oral or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline (PBS), and the suspensions and solutions may contain thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

Treatment of Mammalian Tissues In Vivo

In embodiments in which the method is practiced with cells in vivo in mammals, preferably fibroblasts of the dermis of human skin, or the connective tissue layer underlying the epithelia of the inner wall of the human gastrointestinal tract, by exposing such cells to an adverse-age-effect-ameliorative amount of a 6-(substituted amino)purine cytokinin.

Treatment of Skin

Compositions for use with human skin preferably may be applied once per day or, if necessary to achieve the desired result, more often, to the areas of the skin for which treatment is sought. It is understood that the precise treatment regimen depends upon the individual treated and may be ascertained empirically depending upon the formulation and, particularly, the age of the treated individual. Any regimen is acceptable as long as the desired age-ameliorating effects are achieved without substantial deleterious or sustained undesirable side effects.

The methods for treating human skin are practiced by applying to the skin, preferably daily, a composition of the invention suitable for human skin treatment, as discussed above, for an indefinite period, generally as long as the person desires to enjoy the amelioration of the adverse effects of aging of the skin. Once daily application to the skin of a composition should be required for at least about a month, and up to at least about a year, depending on the age of the person, the condition of the skin to which the composition is applied, and the concentration (or weight fraction) of the 6-(substituted amino)purine cytokinin in the composition, before the beneficial effects, delaying age-related morphological changes in fibroblasts of the basal cell layer of the skin, begin to become apparent at the skin surface. If application of the is terminated, the aging effects ameliorated by the method will again ensue after some time.

For fibroblasts (or other active cells, such as keratinocytes) of the human skin, the method is practiced by applying to the outer surface of the skin a composition that is formulated as a physiologically acceptable cream, ointment, lotion, gel, solution, perfume, solid, or other suitable form for application to the outer surface of the skin that contains one or more 6-(substituted amino)purine cytokinins in a suitable vehicle at an effective concentration deliver to the dermis of the skin an effective concentration effective for ameliorating the adverse effects of aging on active cells (e.g., fibroblasts) in the dermis, whereby the treated skin ages more slowly than untreated skin, becomes younger in appearance than prior to treatment as manifested by a reduction in wrinkling and/or sagging or other cosmetic indicators of age. Such concentrations are such that at least about from 5 ppm to about 0.1% up to about 0.5% is delivered. The precise concentration, which may be empirically determined, is a function of the carrier or delivery vehicle and the form in which the composition is presented to the surface of the skin.

Compositions containing about 0.1% kinetin have been applied to the wrinkled skin of hairless mice exposed to UV light. The skin of treated mice was less wrinkled than the skin of untreated mice and did not exhibit any evidence that the rate of cell growth or total proliferative capacity was altered.

Treatment of Cells of the Gastrointestinal Tract

Generally such exposure will be repeated periodically over the period of time during which it is desired to ameliorate the adverse age effects on the cells. The frequency of exposure will depend on the cells involved, where in the mammal the cells are located (e.g., cells in the gastrointestinal tract, where flushing repeatedly by compositions free of 6-(substituted amino)purine cytokinins occurs, requiring more frequent exposure than cells of the skin), and the concentration of the 6-(substituted amino)purine cytokinin in a concentration range, typically between about 10 ppm and about 1,000 ppm), effective to permeate to the connective tissue layer underlying the epithelia of the inner wall of the gastrointestinal tract at a concentration effective to ameliorate the adverse effects of aging on active cells, such as fibroblasts, in said connective tissue layer.

The following examples are included for illustrative purposes only and are not intended to limit the scope of the invention.

EXAMPLE 1

Formulation and Use of a Composition for Topical Application to the Skin

A composition for topical application to the skin containing the following ingredients by weight %:

| kinetin | 0.1% |
|---|---|
| Oil phase | |
| cetyl alcohol | 5.0% |
| glyceryl monostearate | 15.0% |
| sorbitan monooleate | 0.3% |
| polysorbate 80 USP | 0.3% |
| Aqueous phase | |
| methylcellulose 100 cps | 1.0% |
| methyl paraben | 0.25% |
| propyl paraben | 0.15% |
| purified water q.s. | | has been prepared. The methyl paraben and the propyl paraben were dissolved in hot water after which the methylcellulose was dispersed in the hot water. The mixture was chilled at 6° C. until the methylcellulose was dissolved. The mixture was then heated to 72° C. and added to the oil phase which was heated to 70° C. b stirring continuously. The kinetin was added at 35° C. and the resulting mixture was stirred continuously until dispersed.

This composition is applied to skin on at least a daily basis for as long as the desired age-ameliorating effect is desired.

EXAMPLE 2

Effect of Kinetin on Short-Term Cell Growth

Effects of kinetin on short term growth of normal diploid human embryonic skin fibroblasts, strain designated as KIS, was studied by "one-step growth curve" experiments. For this purpose, equal numbers of KIS cells ($10^5$) were added to several culture flasks containing Dulbecco's modified Eagle's medium (DMEM) supplemented with 10% fetal calf serum, antibiotics and glutamine. Different volumes of stock solutions of kinetin prepared in balanced salt solution (Hank's Buffer) were added to the flasks in order to obtain final concentration of 40 $\mu$M, 80 $\mu$M and 200 $\mu$M kinetin the culture medium. Cultures were then incubated at 37° C. in an atmosphere of 5% $CO_2$. All experiments were done in triplicate.

In order to determine the attachment frequency of cells treated with various doses of kinetin, one set of culture flasks from each dose was used to count the number of cells attached to the bottom surface of the culture flask 6 hours after seeding. This was done by first removing the cells by trypsinization, resuspending them in fresh medium and counting their number using a Coulter counter.

For the estimation of growth rates or proliferation rates of kinetin treated and untreated cells, cell number was determined every 24 hours in each set as above. This was continued until all cultures became confluent and there was no further increase in cell number usually 8–10 days). The following results were obtained:

1. Normal human cells display no adverse morphological effects on treatment with various doses of kinetin as judged by microscopic examination of the cells under a light microscope.

2. Kinetin had no apparent toxic effects on human cells, because there was no difference in cell attachment, cellular debris in the medium and cell number per unit area of culture substratum between treated and untreated cells.

3. Kinetin treated and untreated human cells exhibited the same growth rate and became confluent at the same time. This is clear evidence that kinetin did not increase the growth rates of cells in culture. Further evidence in support this conclusion is presented in Example 3.

EXAMPLE 3

Effect of Kinetin on Long-Term Growth Rate and Total Proliferative Capacity

Effects of kinetin on longer term growth rate and total proliferative capacity of KIS cells were studied by what is known in the art as "longevity curve" experiments. For this purpose, at least sixteen parallel cultures of KIS cells were maintained in the presence of 40 $\mu$M kinetin in the medium, along with an equal number of untreated control cultures. All experiments were started from population doubling level (PDL) six, which is about 12% of the normal life expectancy of the cells that have a total proliferative capacity of the cells of about a PDL=50 in vitro as determined previously.

Methods of cell culture, trypsinization and counting the cell numbers were as described in Example I. For long term studies, however, cultures were serially passaged every time they became confluent. This serial passaging of cultures was continued until all cultures stopped becoming confluent despite weekly changes of culture media for 4–5 weeks. In order to estimate the exact number of PDL achieved by kinetin treated and untreated cultures, cells in at least four confluent culture flasks out of 16 parallel running cultures were subdivided in a split ratio of 1:4, when young, and 1:2, when their growth rate started to slow down due to aging. The number of PDs a culture had undergone between seeding the cells and becoming confluent was determined by: long N/log 2, where N=number of cells in a confluent culture divided by the number of cells seeded originally in that flask. Finally, cumulative PDL for each culture was calculated at the end of their life span in vitro.

In terms of cumulative PDL there was no difference in the life span of human cells grown with or without a continuous presence of kinetin in the culture medium. In this series of experiments, both types of cultures attained a maximum PDL in the range of 47 to 49. This means that the total proliferative capacity of the cells was not significantly changed by the presence of kinetin in the culture medium.

In terms of chronological time, however, kinetin treated cells appeared to live longer (217 days) than the controls (196 days). At the end of their life span, when confluence could no longer be achieved, kinetin treated cells continued to appear much healthier for at least two weeks and without shedding significant numbers of dead cells into the medium.

The slopes of the curves of numbers of population doublings as a function of time (growth rates) for kinetin-treated and untreated cells were experimentally indistinguishable. Thus, the growth rates of the kinetin treated cultures and the untreated control cultures were not significantly different. Kinetin did not significantly alter the genetically determined, inherent limit to normal life span (i.e., total proliferative capacity) of human cells in culture.

DNA Synthesis and Growth Rate

For autoradiography, KIS cells were grown on sterilized glass cover slips either in the presence of different concentrations of kinetin (40 μM to 200 μM) or in its absence. After different durations of treatment, ($^3$H)thymidine (1 microcurie/ml) was added to the cultures either for a short time (2 hours) in order to determine the number of cycling cells at that time, or for longer periods (24–48 hours), to estimate the number of cells in a culture which are capable of entering S phase of the cell cycle. After the completion of the labeling period, cells were processed for autoradiography according to standard methods. At least 500 cells were counted, using a microscope, in each slide after exposure, developing and staining procedures were completed. Percentage of cycling cells (detected autoradiographically as cells with dark nuclei because of the incorporation of radioactive thymidine into newly synthesized DNA) and non-cycling cells were thus determined. Kinetin-treated and untreated cells were found, after labeling 2 hours and longer (24–48 hours), to have experimentally indistinguishable percentages of cycling and non-cycling cells.

Similarly, estimates of $^3$H-thymidine uptake by kinetin-treated and untreated KIS cells, after labeling for either 90 minutes or 72 hours, in terms of dpm from acid-insoluble material per $10^6$ cells measured with a scintillation counter, showed no stimulation of DNA synthesis by treatment with kinetin.

As indicated in Example I, a large number of many independent experiments has shown that kinetin does not induce any additional proliferation of cells in human cell cultures. The experiments of this Example show that kinetin does not stimulate DNA synthesis or push cells into new cell cycles faster than control cells under such cycles. Thus, kinetin does not alter cellular growth rates of human cells.

EXAMPLE 4

Effect of Kinetin on Cellular Morphology

Age-related changes in the morphology of cells during serial passaging is a well-known phenomenon to cell biologists involved with studies of aging. Young human fibroblasts in culture are thin, long, spindle-shaped and are tightly packed in arrays on becoming confluent. Old cells, which have completed more than 90% of life span, are very large in size, very much flattened, irregularly shaped, much vacuolated and contain numerous so-called "residual bodies" which show intense autofluorescence on excitation with ultra-violet rays when observed under a fluorescence microscope.

KIS cells grown in the presence of 40 μM kinetin and grown without kinetin were compared morphologically at PDL=44. The kinetin-treated cells did not have a typical morphology of old cells. Kinetin-treated cells were not significantly larger in size than young (e.g., PDL=14) cells, while the untreated cells were. The kinetin-treated cells maintained a spindle-shaped appearance to a large extent; they were not irregularly placed; and they did not contain as many vacuoles and residual bodies as compared to those without kinetin treatment. This dramatic retention of somewhat youthful appearance, even during the terminal phases of life, is significant evidence for the ability of kinetin, at concentrations on the order of $10^{-6}$ M to $10^{-4}$ M, to delay the onset of age-related symptoms.

In another set of experiments, it was found that cells which had already become old (e.g., PDL greater than 40) could revert morphologically to a somewhat more youthful appearance on addition of kinetin to various concentrations to the culture medium. The degree of reversion depends on the extremity of old age already attained prior to exposure to kinetin, with younger cells reverting further, and on the concentration of kinetin added to the medium and the length of time the kinetin is present. For example, KIS cells with more than 80% life span completed (greater than 40 PDL) began to appear like PDL=30–35 cells after 2–3 weeks with 200 μM kinetin in the culture medium.

The rate of re-acquisition of "old" morphology after kinetin is removed from the medium remains uncertain, but experiments indicate it is much lower than the rate of reversion to younger morphology after kinetin is introduced in to the medium.

Cell Yield and Size

Because cells progressively become larger with age, one parameter of cellular aging in culture is the decline in cell yield (i.e., number of cells in a confluent layer) when cultures approach old age. Therefore, if the area of culture flasks remains the same, the number of cells per flask decreases as cells approach the end of their life span with periodic passaging. One set of cultures of KIS cells was cultured with periodic passaging without kinetin in the media. Another set of cultures of KIS cells was treated the same way except 40 μM of kinetin was included in the media. With the untreated cells, cell yield remained nearly constant at about $1.5 \times 10^{-6}$ per 25 cm$^2$ until PDL=43 and then decreased to about $3.5 \times 10^5$ per 25 cm$^2$ at PDL=48, where growth ceased. The cell yield of the treated cells remained nearly constant at about $1.5 \times 10^6$ per 25 cm$^2$ until PDL=48 and then decreased to about $7 \times 10^5$ per 25 cm$^2$ at PDL=49, where growth ceased. This maintenance of the cell yield characteristic of "young" cells, even during the last phase of life, for cells treated with kinetin is highly significant in terms of delaying the onset of some of the symptoms of aging in human cells by kinetin treatment.

Since modifications will be apparent to those of skill in this art, it is intended that this invention be limited only by the scope of the appended claims.

What is claimed is:

1. A method for treating mammalian skin in order to improve its cosmetic appearance, said method comprising topically applying to said mammalian skin an effective amount of one or more 6-(substituted amino)purine cytokinins, wherein the amount applied is sufficient to improve the cosmetic appearance of said mammalian skin but does not alter the growth rate and total proliferative capacity of the mammalian skin cells.

2. The method of claim 1, wherein the improvement in cosmetic appearance is manifested by a reduction in the number or depth of wrinkles in said mammalian skin or by a delay in the development of wrinkles in said mammalian skin and wherein said 6-(substituted amino)-purine cytokinin is contained in a lotion, ointment, cream, or gel suitable for topical application to said mammalian skin.

3. The method of claim 1, wherein the mammalian skin to be treated is human skin.

4. The method of claim 2, wherein the mammalian skin to be treated is human skin.

5. The method of claim 3, wherein the 6-(substituted amino)purine cytokinins are of general formula

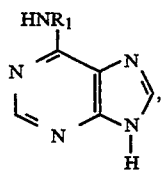

wherein R₁ is a radical selected from the group consisting of furfuryl radical, phenyl radical, benzyl radical, n-alkyl and branched alkyl radicals containing 4, 5, or 6 carbon atoms, (cyclohexyl)methyl radical, and 3-hydroxymethyl-3-methylallyl radical.

6. The method of claim 4, wherein the 6-(substituted amino)purine cytokinins are of general formula

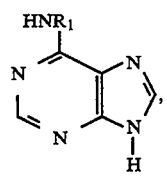

wherein R₁ is a radical selected from the group consisting of furfuryl radical, phenyl radical, benzyl radical, n-alkyl and branched alkyl radicals containing 4, 5, or 6 carbon atoms, (cyclohexyl) methyl radical, and 3-hydroxymethyl-3-methylallyl radical.

7. The method of claim 5, wherein R₁ is the furfuryl radical.

8. The method of claim 6, wherein R₁ is the furfuryl radical.

9. The method of claim 5, wherein R₁ is the 3-hydroxymethyl-3-methylallyl radical.

10. The method of claim 6, wherein R₁ is the 3-hydroxymethyl-3-methylallyl radical.

11. The method of claim 5, wherein the amount of 6-(substituted amino)purine cytokinins in the lotion, ointment, cream, or gel is in the range of about 50 ppm to about 1,000 ppm.

12. The method of claim 6, wherein the amount of 6-(substituted amino)purine cytokinins in the lotion, ointment, cream, or gel is in the range of about 50 ppm to about 1,000 ppm.

13. A method for treating human skin in order to improve its cosmetic appearance, said method comprising topically applying to said human skin a composition containing an amount of one or more 6-(substituted amino)purine cytokinins sufficient to improve the cosmetic appearance of said human skin, wherein the 6-(substituted amino)purine cytokinins do not significantly alter the growth rate and total proliferative capacity of the human skin cells and wherein the improvement in cosmetic appearance is manifested by a reduction in the number or depth of wrinkles in said human skin or by a delay in the development of wrinkles in said human skin.

14. The method of claim 13, wherein the composition is a lotion, ointment, cream, or gel suitable for topical application.

15. The method of claim 13, wherein the 6-(substituted amino)purine cytokinins are of general formula

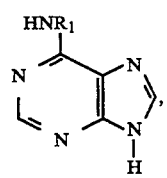

wherein R₁ is a radical selected from the group consisting of furfuryl radical, phenyl radical, benzyl radical, n-alkyl and branched alkyl radicals containing 4, 5, or 6 carbon atoms, (cyclohexyl)methyl radical, and 3-hydroxymethyl-3-methylallyl radical.

16. The method of claim 15, wherein the composition is a lotion, ointment, cream, or gel suitable for topical application.

17. The method of claim 15, wherein R₁ is the furfuryl radical.

18. The method of claim 15, wherein R₁ is the 3-hydroxymethyl-3-methylallyl radical.

19. The method of claim 15, wherein the amount of 6-(substituted amino)purine cytokinins in the composition is in the range of about 10 ppm and about 5,000 ppm.

20. The method of claim 15, wherein the amount of 6-(substituted amino)purine cytokinins in the composition is in the range of about 100 ppm and about 1,000 ppm.

* * * * *